(12) United States Patent
Skarsgard et al.

(10) Patent No.: US 12,036,120 B1
(45) Date of Patent: Jul. 16, 2024

(54) LOCK DELIVERY SYSTEM

(71) Applicant: Vesalius Cardiovascular Inc., Vancouver (CA)

(72) Inventors: Peter Lloyd Skarsgard, Vancouver (CA); Colm O'Sullivan, Vancouver (CA); Ryan Harrington, Vancouver (CA)

(73) Assignee: VESALIUS CARDIOVASCULAR INC., Vancouver (CA)

( * ) Notice: Subject to any disclaimer, the term of this patent is extended or adjusted under 35 U.S.C. 154(b) by 0 days.

(21) Appl. No.: 18/458,360

(22) Filed: Aug. 30, 2023

(51) Int. Cl.
*A61F 2/24* (2006.01)
*A44B 17/00* (2006.01)
*F16B 21/06* (2006.01)
*F16B 21/07* (2006.01)
*A61B 17/04* (2006.01)

(52) U.S. Cl.
CPC .......... *A61F 2/2442* (2013.01); *A44B 17/0011* (2013.01); *A61B 17/0401* (2013.01); *A61B 2017/0403* (2013.01); *A61B 2017/0406* (2013.01); *A61B 17/0487* (2013.01); *A61F 2220/0091* (2013.01); *F16B 21/06* (2013.01); *F16B 21/065* (2013.01); *F16B 21/073* (2013.01); *F16B 21/078* (2013.01)

(58) Field of Classification Search
CPC .......... A61F 2/2442; A61F 2220/0091; A61B 17/0401; A61B 17/0487; A61B 2017/0406; A61B 2017/0403; A44B 17/0011; F16B 21/065; F16B 21/06; F16B 21/078; F16B 21/073
See application file for complete search history.

(56) References Cited

U.S. PATENT DOCUMENTS

| 5,148,578 | A | * | 9/1992 | Clarke | ............... | A41F 17/00 24/41.1 |
| 7,027,851 | B2 | | 4/2006 | Mejia | | |
| 8,652,202 | B2 | | 2/2014 | Alon et al. | | |
| 9,044,221 | B2 | | 6/2015 | Zentgraf et al. | | |

(Continued)

FOREIGN PATENT DOCUMENTS

| WO | 2003037227 A2 | 5/2003 |
| WO | 2013037805 A1 | 3/2013 |

(Continued)

*Primary Examiner* — Jing Rui Ou
(74) *Attorney, Agent, or Firm* — Oyen Wiggs Green & Mutala LLP

(57) ABSTRACT

A lock delivery system is disclosed. The lock mechanism is reversible between an unlocked configuration and a locked configuration. The lock mechanism may comprise a casing, and a first body and a second body arranged spaced-apart in the casing. The first body may comprise a first gripping portion extending to a first actuating arm, and a first spring arranged spaced-apart from the first actuating arm. The second body may comprise a second gripping portion extending to a second actuating arm, and a second spring arranged spaced-apart from the second actuating arm. The first and second bodies are each pivotable about a respective first pivot point and second pivot point so as to move the lock mechanism between an unlocked configuration and a locked configuration. A lock delivery catheter may be used as a means to move the lock mechanism between the unlocked configuration and the locked configuration.

19 Claims, 4 Drawing Sheets

(56) References Cited

U.S. PATENT DOCUMENTS

| | | | |
|---|---|---|---|
| 9,295,553 | B2 | 3/2016 | Padala et al. |
| 10,039,531 | B2 | 8/2018 | Yoganathan et al. |
| 10,206,673 | B2 * | 2/2019 | Maisano ............ A61B 17/0487 |
| 10,206,776 | B2 | 2/2019 | Alon |
| 10,238,495 | B2 | 3/2019 | Marsot et al. |
| 10,856,983 | B2 | 12/2020 | Keränen et al. |
| 11,109,972 | B2 | 9/2021 | Marsot et al. |
| 2003/0167071 | A1 * | 9/2003 | Martin ................ A61B 17/0487 606/232 |
| 2004/0181238 | A1 * | 9/2004 | Zarbatany .......... A61B 17/0467 606/108 |
| 2005/0004665 | A1 | 1/2005 | Aklog |
| 2005/0075727 | A1 | 4/2005 | Wheatley |
| 2006/0282083 | A1 * | 12/2006 | Fanton ................ A61B 17/0401 606/232 |
| 2010/0030330 | A1 | 2/2010 | Bobo et al. |
| 2010/0049313 | A1 | 2/2010 | Alon et al. |
| 2012/0184971 | A1 | 7/2012 | Zentgraf et al. |
| 2014/0194716 | A1 | 7/2014 | Diep et al. |
| 2015/0162671 | A1 * | 6/2015 | Hoppmann ........ H01R 4/48365 439/370 |
| 2016/0367360 | A1 | 12/2016 | Cartledge et al. |
| 2019/0053902 | A1 | 2/2019 | Zentgraf et al. |
| 2021/0052387 | A1 | 2/2021 | Greenan et al. |

FOREIGN PATENT DOCUMENTS

| | | | |
|---|---|---|---|
| WO | 2015017689 | A1 | 2/2015 |
| WO | 2015195823 | A1 | 12/2015 |
| WO | 2020146548 | A1 | 7/2020 |
| WO | 2020154797 | A1 | 8/2020 |

\* cited by examiner

LOCK DELIVERY SYSTEM

FIELD OF THE INVENTION

The invention pertains to a lock delivery system, and in particular, one for use in tissues of a subject.

BACKGROUND OF THE INVENTION

Lock delivery systems for use in tissues of a subject, such as a human subject, are known in the art. Conventional lock delivery systems are difficult to use, and are not reversible, such that when a lock mechanism is secured in position, it cannot be moved. There is a need for an improved lock delivery system for use in tissues of a subject.

SUMMARY

One aspect of the invention provides a lock delivery system. The lock delivery system comprises a lock mechanism. The lock mechanism may be used in tissues of a subject. The lock mechanism is reversible between an unlocked configuration and a locked configuration. The lock mechanism may comprise a casing, and a first body and a second body arranged spaced-apart in the casing. The first body may comprise a first gripping portion extending to a first actuating arm, and a first spring arranged spaced-apart from the first actuating arm. The second body may comprise a second gripping portion extending to a second actuating arm, and a second spring arranged spaced-apart from the second actuating arm. The first and second bodies are each pivotable about a respective first pivot point and second pivot point so as to move the lock mechanism between an unlocked configuration and a locked configuration. The first and second pivot points may be secured to a bottom case of the casing.

In some embodiments, the first gripping portion and the second gripping portion each comprises a plurality of teeth. The plurality of teeth of the first gripping portion may be arranged to face the plurality of teeth of the second gripping portion.

In some embodiments, the means for pivoting the first and second bodies of the lock mechanism comprises a lock delivery catheter. The lock delivery catheter may comprise a body defined by a lumen, and a pushable rod slideable longitudinally within the lumen to move between a withdrawn position and an advanced position. The pushable rod may project outwardly from a distal end of the body in the advanced position. In some embodiments, at least a portion of the pushable rod is dimensioned to snuggly fit between the first and second actuating arms of the lock mechanism, thereby pushing the actuating arms away from each other to move the lock mechanism from the locked configuration to the unlocked configuration.

In some embodiments, the body comprises a proximal end and extends distally to a first arm and a second arm. In such embodiments, the terminal ends of the first and second arms form the distal end of the body. Attachment members may be arranged to project from each of the terminal ends of the first and second arms. The attachment members may be dimensioned to engage a groove wall defined within the groove of the lock mechanism, thereby securing the lock delivery catheter to the lock mechanism for facilitating advancement of the pushable rod within the lock mechanism.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Figure 1:
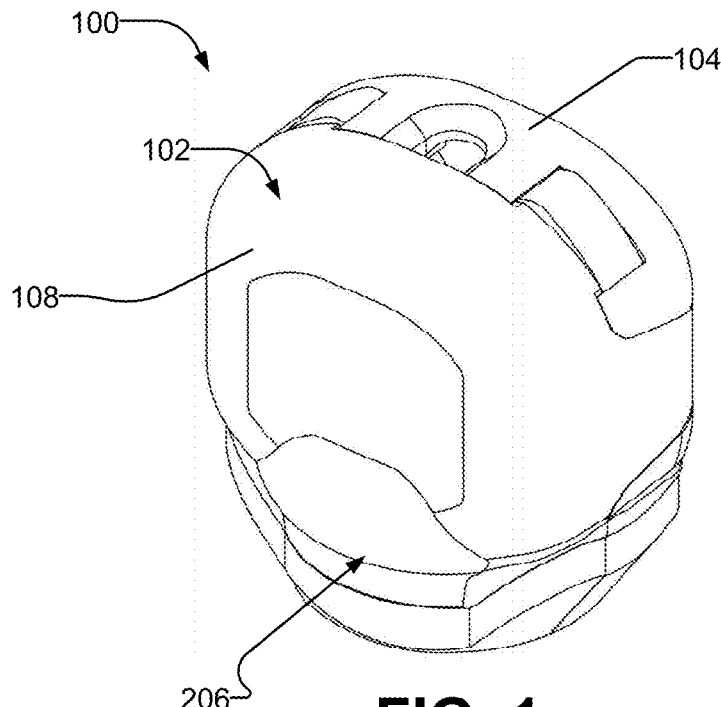
FIG. 1 is a perspective view illustrating a lock mechanism of a lock delivery system according to an example embodiment of the invention.
Figure 2:
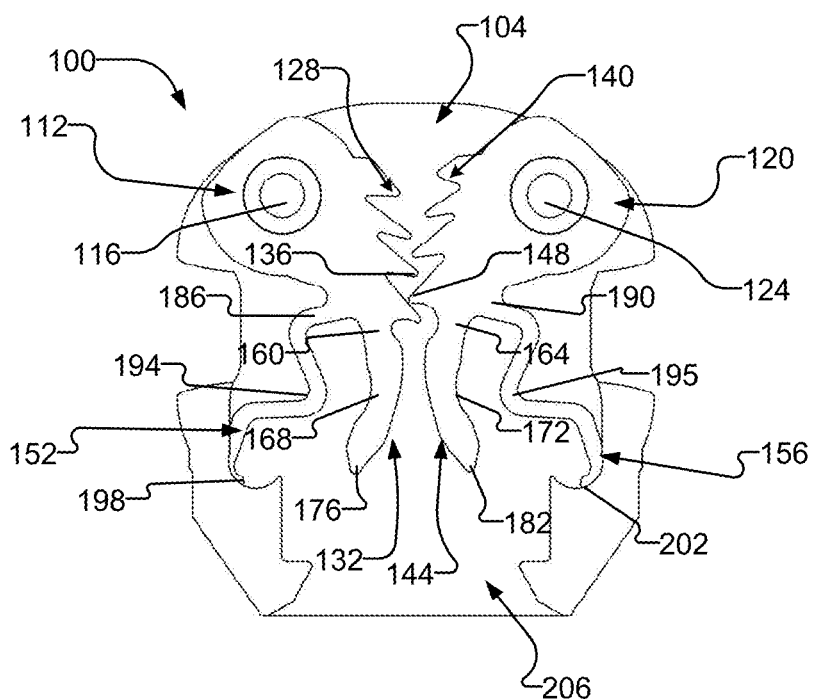
FIG. 2 is a top elevational view of the interior of the FIG. 1 lock mechanism, showing the lock mechanism in a rest state.
Figure 3:
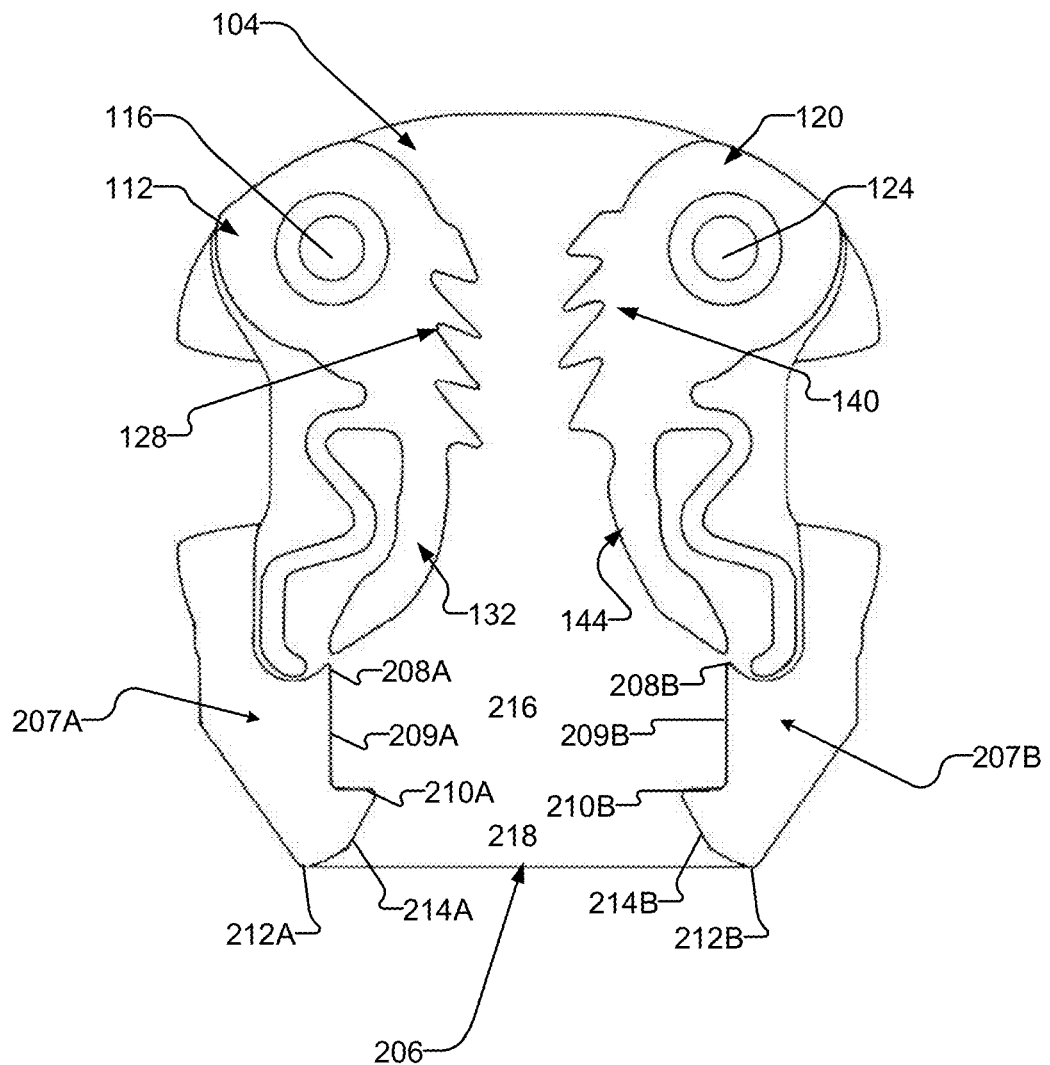
FIG. 3 is a top elevational view of the interior of the FIG. 1 lock mechanism, showing the lock mechanism in an unlocked configuration.

Referring to FIGS. 1-3, an embodiment of the invention is a lock delivery system 10. The lock delivery system 10 comprises a lock mechanism 100. The lock mechanism is reversible between an unlocked configuration and a locked configuration. One non-limiting example application of the lock delivery system is in the field of cardiovascular valve repair, such as the repair of the mitral valves. The lock mechanism may be used to secure a tether coupled with a plurality of anchors so as to draw the anchors together, for example to tighten sections of a tissue, such as the mitral annulus. The anchors may for example be used to secure a repair device to the mitral annulus.

The lock mechanism 100 comprises a casing 102 with a bottom case 104 and a top case 108 arranged to be placed on the bottom case 104. A first body 112 may be secured to the bottom case 104 by a first pivot point 116, and a second body 120 may be secured to the bottom case 104 by a second pivot point 124. The first and second pivot points 116, 124 may be secured to the bottom case 104. The first and second pivot points 116, 124 are positioned spaced-apart on the bottom case 104. The first body 112 may be aligned on the same plane as the second body 120.

The first body 112 comprises a first gripping section 128, extending to a first actuating arm 132. The first gripping section 128 may comprise a plurality of first teeth 136. The second body 120 comprises a second gripping section 140, extending to a second actuating arm 144. The second gripping section 140 may comprise a plurality of second teeth 148. The first gripping section 128 may be arranged to face the second gripping section 140. In some embodiments, the first teeth 136 is arranged to face the second teeth 148, each of the teeth 136, 148 protruding towards one another.

In the illustrated embodiments, the first and second teeth 136, 148 are arranged offset from each other.

In some embodiments, the first and second actuating arms 132, 144 each extends from a first end 160, 164 proximate to the respective gripping section 128, 140, towards a respective curved portion 168, 172, and therefrom extends to a second end 176, 182. In some example embodiments, the curved portion 168 of the first actuating arm 132 comprises a convex shape, and the curved portion 172 of the second actuating arm 144 comprises a concave shape.

The first body 112 comprises a first spring 152 arranged spaced-apart from the first actuating arm 132, at a side opposite to the second body 120. The second body 120 comprises a second spring 156 arranged spaced-apart from the second actuating arm 144, at a side opposite to the first body 112. The first and second springs 152, 156 may each extend from a first end 186, 190, proximate to the respective actuating arm 132, 144, to one or more bent points 194, 195 and therefrom continually extends to an opposing second end 198, 202. The second end 198 of the first spring 152 may be arranged spaced-apart from the second end 176 of the first actuating arm 132. The second end 190 of the second spring 156 may be arranged spaced-apart from the second end 182 of the second actuating arm 144. In the illustrated embodiments, the first and/or second spring 152, 156 comprises four bent points 194, 195. The number of bent points 194, 195 along the spring 152, 156 may however be adjusted depending on the length of the spring and/or the amount of force desired to be exerted by the spring.

In some embodiments, the first gripping portion, the first actuating arm, and the first spring are integrally formed from one piece of material, and the second gripping portion, the second actuating arm, and the second spring are integrally formed from one piece of material.

The bodies 112, 120 are pivotable, about the respective first and second pivot points 116, 124, between an unlocked configuration and a locked configuration. The bodies 112, 120 are in the locked configuration at a state of rest. In the locked configuration, a gap distance between the actuating arms 132, 144 is at a minimum, and in the unlocked configuration, the gap distance between the actuating arms 132, 144 is at a maximum. In some example embodiment, the bodies 112, 120 pivot to the unlocked configuration to allow passage of a tether, and once the tether is in a desired position, the bodies 112, 120 pivot to the locked configuration to secure the tether at the desired position.

Means may be provided to pivot the bodies 112, 120 between the unlocked configuration and the locked configuration. The means may comprise a pushable rod dimensioned to extend between the actuating arms 132, 144, snuggly fitted therebetween, for moving the actuating arms 132, 144 away from each other, thereby pushing the gripping sections 128, 140 away from each other to allow movement of the material, e.g., a tether, to be secured between the gripping sections 128, 140. The lock mechanism 100 is reversible between the unlocked configuration and the locked configuration by pivoting the bodies 112, 120 between the two configurations.

In some example embodiments, the means comprises a lock delivery catheter. The lock delivery catheter may for example comprise a dilater or a pushable rod, which may be selectively moveable to project distally outwardly of the catheter.

In some embodiments, a groove 206 is defined by the bottom case 104 and/or top case 108, dimensioned to receive the pushable rod or a portion thereof. The groove 206 may be positioned proximal to the first and second actuating arms 132, 144. The groove 206 may facilitate the insertion of the pushable rod into the lock mechanism 100 so as to pivote the bodies 112, 120. In some embodiments, the cross-sectional shape of the groove 206 is circular, or substantially circular. A circular groove may advantageously facilitate engagement with a lock delivery catheter, without the need for the lock delivery catheter to be positioned at a particular orientation relative to the groove. The lock delivery catheter may engage with a circular groove 206 at any possible radial orientation.

Referring to FIG. 3, in some embodiments, the groove 206 is defined by a continuous groove wall 207. The continuous groove wall 207 may be circular or substantially circular. The continuous groove wall 207 may comprise a first wall portion 207A and a second wall portion 207B each projecting inwardly towards a central longitudinal axis of the groove 206. In some embodiments, the first and second wall portions 207A,B are disposed radially opposite to each other with respect to the central longitudinal axis of the groove 206. The first and second wall portions 207A,B each extends from a first point 208A,B along a first section 209A,B to an intermediate section 210A,B, and therefrom towards a second point 212A,B along a second section 214A,B. The space between the first sections 209A,B of the wall portions 207A,B define an inner section 216, and the space between the second sections 214A,B of the wall portions 207A,B define an outer section 218. In some embodiments, the diameter of the inner section 216 (as defined by the distance between the first sections 209A,B) is greater than the diameter of the outer section 218 (as defined by the distance between the second sections 214A,B). In some embodiments, the intermediate section 210A,B may be arranged at an angle projecting from the first section 209A, B. In some example embodiment, the angle is between about 5° to about 120°, and in some embodiments, between about 20° to about 110°, and in some embodiments, between about 40° to about 100°, in some embodiments, between about 60° to about 100°, and in some embodiments, between about 70° to about 95°. In some embodiments, the intermediate section 210A,B is oriented to provide a means for attachment for a pushable rod. The intermediate section 210A,B may also be oriented to provide a counterforce to the force applied by the pushable rod during advancement.

Figure 5A:
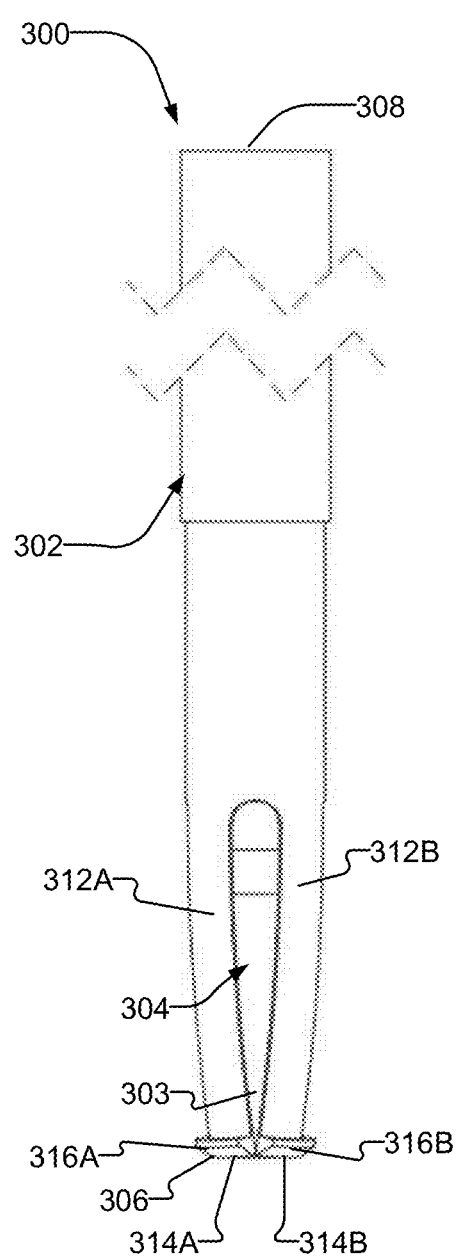
FIG. 5A is a top elevational view of the FIGS. 4A and 4B lock delivery catheter, showing the lock delivery catheter in a relax configuration.
Figure 5B:
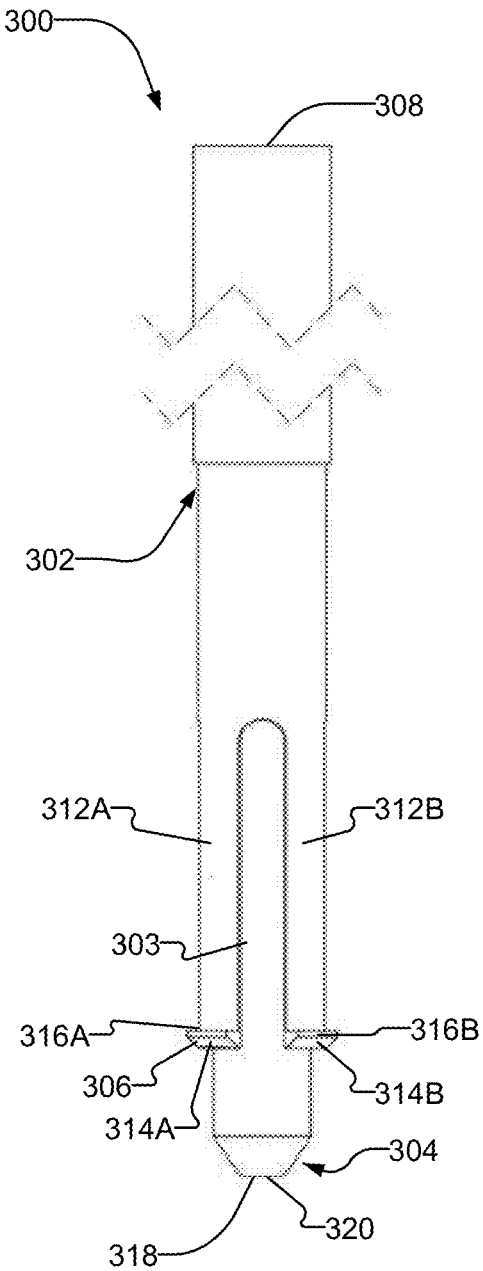
FIG. 5B is a top elevational view of the FIGS. 4A and 4B lock delivery catheter, showing the lock delivery catheter in an activated configuration.

FIGS. 5A and 5B illustrate an example pushable rod that may be used with the lock mechanism 100. FIGS. 5A and 5B illustrate an example lock delivery catheter 300 that may be used to move the lock mechanism 100 between the unlocked configuration and the locked configuration. FIG. 5A illustrates the lock delivery catheter 300 in a relaxed configuration, and FIG. 5B illustrates the lock delivery catheter in an activated configuration.

The lock delivery catheter 300 comprises a body 302 defined by a lumen 303, and a pushable rod 304 slideable within the lumen 303. The pushable rod 304 is slideable longitudinally within the lumen 303, between a withdrawn position (FIG. 5A) and an advanced position (FIG. 5B). In the withdrawn position, the pushable rod 304 is received within the lumen 303. In the advanced position, the pushable rod 304 projects outwardly from a distal end 306 of the body 302. At least a portion of the pushable rod 304 may be dimensioned to snuggly fit between the first and second actuating arms 132, 144 of the locking mechanism 100 so as to move the actuating arms 132, 144 away from each other, thereby pushing the gripping sections 128, 140 away from each other.

In some embodiments, the body 302 comprises a proximal end 308 and extends distally to a first arm 312A and a second arm 312B. In such embodiments, the terminal ends 314A,B of the first and second arms 312A,B form the distal end 306 of the body 302. Means may be arranged to secure the body 302 to the lock mechanism 100 to facilitate moving the lock mechanism 100 from the locked configuration to the unlocked configuration. In some embodiments, such means comprises an attachment member 316A,B projecting from each of the terminal ends 314A,B of the first and second arms 312A,B. The attachment members 316A,B may be dimensioned to engage with the first and second wall portions 207A,B within the groove 206 of the locking mechanism 100. In some embodiments, the attachment members 316A,B are dimensioned to engage with the intermediate sections 210A,B of the first and second wall portions 207A,B so as to secure the body 302 to the locking mechanism 100. In some example embodiments, the attachment members 316A,B each comprises a mounting ridge projecting axially outwardly from the wall of the respective first and second arms 312A,B at the terminal ends 314A,B thereof.

The first and second arms 312A,B may be moveable laterally when the lock delivery catheter 300 moves between the relaxed configuration and the activated configuration. The distance between the first and second arms 312A,B is at a minimum when the body 302 is in the relaxed configuration, and at a maximum when the body 302 in the fully activated configuration. In some example use embodiments, referring to FIGS. 4A and 4B, when the body 302 is in the relaxed configuration, the distance between the first and second arms 312A,B is less than the diameter of the outer section 218 of the groove 206 of the locking mechanism 100 so that the attachment members 316A,B may be inserted into the groove 206 (FIG. 4B). Once inserted into the groove 206, the pushable rod 304 may be extended into the advanced position, thereby increasing the distance between the first and second arms 312A,B so as to move the body 302 into the activated configuration. When the body 302 is in the activated configuration, the distance between the first and second arms 312A,B is greater than the diameter of the outer section 218 of the groove 206, allowing the attachment members 316A,B to move into engagement with the respective intermediate sections 210A,B of the first and second wall portions 207A,B thereby securing the body 302 to the lock mechanism 100 (FIG. 4A).

The illustrated embodiments show that the body 302 comprises a pair of arms (first and second arms 312A,B); this is not mandatory. The body 302 may comprise any number of arms 312. In some embodiments, the number of arms 312 of the body 302 correspond to the number of wall portions 207A,B provided on the continuous groove wall 207 of the groove 206. In embodiments in which more than two wall portions 207A,B are provided, the wall portions are arranged radially spaced-apart in respect of the central longitudinal axis of the groove 206, each projecting inwardly towards the central longitudinal axis, facing each other.

In example use embodiments, a tether may be arranged to pass through a lumen 318 of the pushable rod 304. The tether may be advanced longitudinally from a distal end 320 of the pushable rod 304. The tether may be arranged to be advanced between the first and second bodies 112, 120 of the lock mechanism 100, and be secured between the first and second gripping sections 128, 140.

Figure 4A:
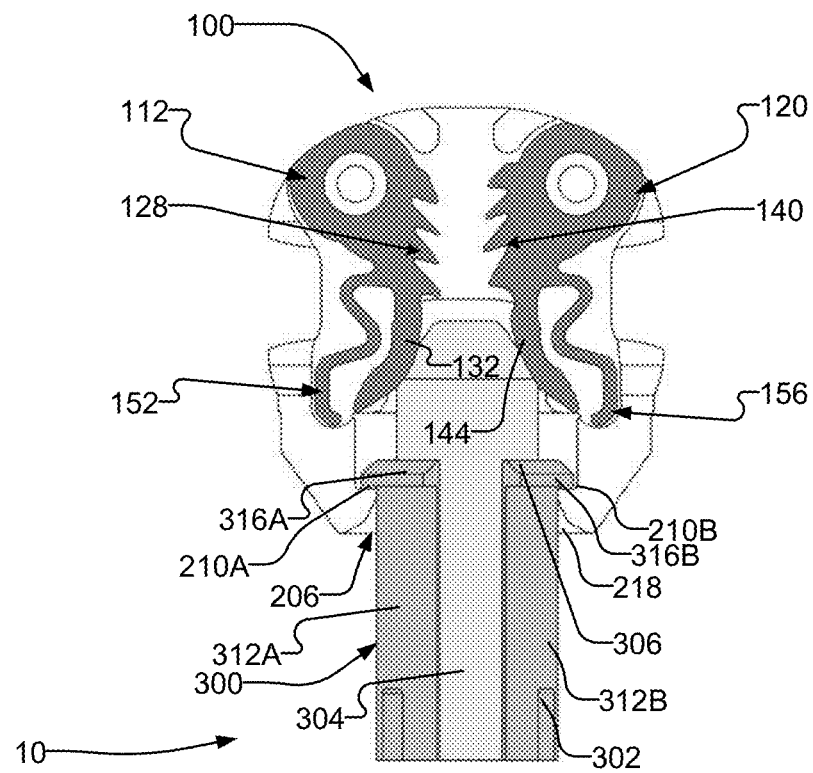
FIG. 4A is a top elevational view of a lock delivery catheter in an activated configuration, showing the lock delivery catheter engaged with the FIG. 1 lock mechanism in the unlocked configuration.
Figure 4B:
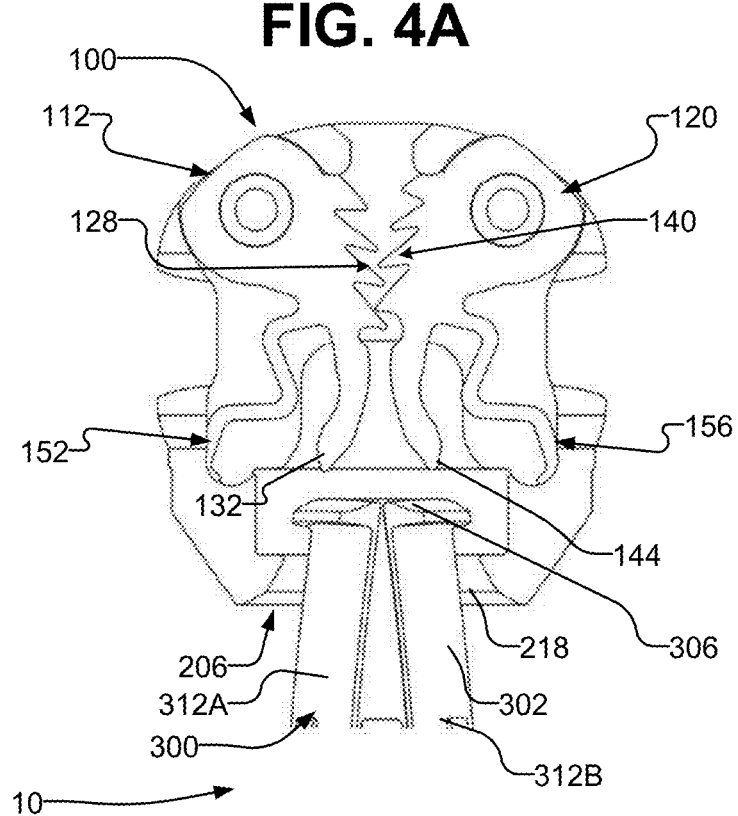
FIG. 4B is a top elevational view of the FIG. 4A lock delivery catheter in a relaxed configuration, showing the lock delivery catheter inserted within a groove of the FIG. 1 lock mechanism in the locked configuration.

Referring to FIGS. 4A and 4B, in an example method, the distal end 306 of the body 302 of the lock delivery catheter 300 is inserted into the groove 206 of the lock mechanism 100. At this stage, the lock delivery catheter 300 is in the relaxed configuration and the pushable rod 304 is in the withdrawn position. The lock mechanism 100 is in the locked configuration, The pushable rod 304 is then moved to an advanced position so as to move the lock delivery catheter 300 into the activated configuration. The advancement of the pushable rod 304 moves the attachment members 316A,B on the first and second arms 312A,B of the body 302 into engagement with the intermediate sections 210A,B of the first and second wall portions 207A,B within the groove 206, thereby securing the body 302 to the lock mechanism 100. Once the body 302 is secured to the lock mechanism 100, the pushable rod 304, having a tether advanced longitudinally therefrom, is then further advanced distally, engaging the actuating arms 132, 144 of the first and second bodies 112, 120 of the lock mechanism 100, thereby pushing the arms 132, 144 away from one another to move the lock mechanism 100 into the unlock configuration. The tether may then slide between the first and second gripping sections 128, 140 of the first and second bodies 112, 120 of the lock mechanism 100. The pushable rod is then moved to the withdrawn position. Moving the pushable rod 304 to the withdrawn position releases the engagement of the rod 304 with the actuating arms 132, 144, thereby allowing the actuating arms 132, 144 to move to the state of rest. Moving the pushable rod 304 into the withdrawn position also releases the engagement between the attachment members 316A,B on the first and second arms 312A,B of the body 302 and the intermediate sections 210A,B of the first and second wall portions 207A,B within the groove 206, allowing the lock delivery catheter 300 to withdraw from the groove 206 of the lock mechanism 100. The lock delivery catheter 300 thus functions to move the lock mechanism 100 between the unlocked and locked configurations reversibly.

Throughout the foregoing description and the drawings, in which corresponding and like parts are identified by the same reference characters, specific details have been set forth in order to provide a more thorough understanding to persons skilled in the art. However, well known elements may not have been shown or described in detail or at all to avoid unnecessarily obscuring the disclosure.

As will be apparent to those skilled in the art in the light of the foregoing disclosure, many alterations and modifications are possible in the practice of this invention without departing from the scope thereof. Accordingly, the description and drawings are to be regarded in an illustrative, rather than a restrictive, sense.

The invention claimed is:
1. A lock mechanism comprising:
   a casing (102); and
   a first (112) and a second (120) body arranged spaced-apart inside the casing, the first body comprising a first gripping portion (128) extending to a first actuating arm (132), and a first spring (152) arranged spaced-apart from the first actuating arm (132), the second body comprising a second gripping portion (140) extending to a second actuating arm (144), and a second spring (156) arranged spaced-apart from the second actuating arm, wherein the first and second gripping portions each comprises a plurality of teeth (136, 148), the plurality of teeth of the first gripping portion arranged to face the plurality of teeth of the second gripping portion,
   and wherein the first and second bodies are each pivotable about a respective first pivot point (116) and second pivot point (124) so as to move the lock mechanism between an unlocked configuration and a locked configuration.

2. The lock mechanism as defined in claim 1, wherein a gap distance between the first and second actuating arms is at a minimum when the lock mechanism is in the locked configuration, and the gap distance between the first and second actuating arms is at a maximum when the lock mechanism is in the unlocked configuration.

3. The lock mechanism as defined in claim 1, wherein the first and second actuating arms each extends from a first end (160, 164) to a curved portion (168, 172), and therefrom continually extends to a second end (176, 182).

4. The lock mechanism as defined in claim 3, wherein the curved portion of the first actuating arm comprises a convex shape, and the curved portion of the second actuating arm comprises a concave shape.

5. The lock mechanism as defined in claim 1, wherein the first and second springs each extends from a first end (186, 190) to one or more bent points (194), and therefrom continually extends to a second end (198, 202).

6. The lock mechanism as defined in claim 5, wherein the first and second springs each comprises four bent points.

7. The lock mechanism as defined in claim 1, wherein the casing comprises a bottom case (104) and a top case (108).

8. The lock mechanism as defined in claim 7, wherein the first and second pivot points are secured to the bottom case.

9. The lock mechanism as defined in claim 7, wherein the bottom case defines a groove (206) between the first and second actuating arms proximate to second ends thereof.

10. A lock mechanism comprising:
a casing (102); and
a first (112) and a second (120) body arranged spaced-apart inside the casing, the first body comprising a first gripping portion (128) extending to a first actuating arm (132), and a first spring (152) arranged spaced-apart from the first actuating arm (132), the second body comprising a second gripping portion (140) extending to a second actuating arm (144), and a second spring (156) arranged spaced-apart from the second actuating arm,
wherein the first and second bodies are each pivotable about a respective first pivot point (116) and second pivot point (124) so as to move the lock mechanism between an unlocked configuration and a locked configuration,
and wherein the first gripping portion, the first actuating arm, and the first spring are integrally formed, and wherein the second gripping portion, the second actuating arm, and the second spring are integrally formed.

11. The lock mechanism as defined in claim 10, wherein the first and second gripping portions each comprises a plurality of teeth (136, 148), the plurality of teeth of the first gripping portion arranged to face the plurality of teeth of the second gripping portion.

12. The lock mechanism as defined in claim 10, wherein a gap distance between the first and second actuating arms is at a minimum when the lock mechanism is in the locked configuration, and the gap distance between the first and second actuating arms is at a maximum when the lock mechanism is in the unlocked configuration.

13. The lock mechanism as defined in claim 10, wherein the first and second actuating arms each extends from a first end (160, 164) to a curved portion (168, 172), and therefrom continually extends to a second end (176, 182).

14. The lock mechanism as defined in claim 13, wherein the curved portion of the first actuating arm comprises a convex shape, and the curved portion of the second actuating arm comprises a concave shape.

15. The lock mechanism as defined in claim 10, wherein the first and second springs each extends from a first end (186, 190) to one or more bent points (194), and therefrom continually extends to a second end (198, 202).

16. The lock mechanism as defined in claim 15, wherein the first and second springs each comprises four bent points.

17. The lock mechanism as defined in claim 10, wherein the casing comprises a bottom case (104) and a top case (108).

18. The lock mechanism as defined in claim 17, wherein the first and second pivot points are secured to the bottom case.

19. The lock mechanism as defined in claim 17, wherein the bottom case defines a groove (206) between the first and second actuating arms proximate to second ends thereof.

* * * * *